United States Patent [19]

Eggerer et al.

[11] Patent Number: 4,609,673
[45] Date of Patent: Sep. 2, 1986

[54] CARBOXYLIC ACID DERIVATIVES, PROCESSES FOR THE PREPARATION THEREOF AND PHARMACEUTICAL COMPOSITIONS CONTAINING THEM

[75] Inventors: Hermann Eggerer, Planegg; Bernd Hagenbruch, Lampertheim; Tran G. Nguyen, Mannheim; Karlheinz Stegmeier, Heppenheim; Johannes Pill, Leimen, all of Fed. Rep. of Germany

[73] Assignee: Boehringer Mannheim GmbH, Mannheim, Fed. Rep. of Germany

[21] Appl. No.: 682,935

[22] Filed: Dec. 18, 1984

[30] Foreign Application Priority Data

Jan. 10, 1984 [DE] Fed. Rep. of Germany ....... 3400514

[51] Int. Cl.$^4$ ............... C07C 149/20; C07C 147/05; A61K 31/22
[52] U.S. Cl. .................................... 514/542; 514/529; 562/503; 562/505; 514/530; 562/506; 562/507; 514/531; 562/556; 564/154; 514/533; 514/538; 514/546; 514/547; 514/549; 514/550; 514/554; 514/555; 514/562; 560/12; 560/13; 560/16; 560/105; 560/121; 560/123; 560/124; 560/125; 560/148; 560/150; 560/151; 560/153; 560/184; 560/226; 560/250; 560/251; 560/252; 560/253; 562/426; 562/430
[58] Field of Search ............... 562/556, 507, 426, 430, 562/503, 505, 506; 560/12, 13, 16, 125, 150, 153, 250, 251, 252, 253, 121, 123, 124, 151; 514/529, 541, 538, 550, 554, 555, 562, 530, 531, 533, 542, 547, 549, 546

Primary Examiner—Michael L. Shippen
Attorney, Agent, or Firm—Felfe & Lynch

[57] ABSTRACT

The present invention provides carboxylic acid derivatives of the general formula:

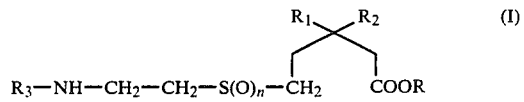

wherein R is a hydrogen atom, alkyl, a metal cation or an ammonium or alkylammonium ion, $R_1$ is a hydrogen atom, a hydroxyl group or an alkyl, O-alkyl,O-benzyl or O-acyl radical, $R_2$ is a hydrogen atom or an alkyl, aryl or aralkyl radical, n is 0, 1 or 2 and $R_3$ is an acyl radical, this radical being (a) a straight-chained or branched, saturated or unsaturated alkanoyl radical containing 2 to 11 carbon atoms; or (b) the radical

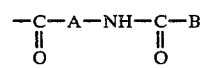

in which A is a straight-chained or branched, saturated or unsaturated aliphatic hydrocarbon radical containing up to 4 carbon atoms, which is optionally substituted by hydroxyl, and B is a straight-chained or branched, saturated or unsaturated aliphatic hydrocarbon radical containing up to 8 carbon atoms, which is optionally substituted one or more times by hydroxyl, carboxyl or phenyl, or B is a phenyl or cycloalkyl radical; or (c) the radical

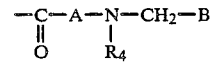

in which A and B have the same meanings as in (b) and $R_4$ is a hydrogen atom or an alkyl or aralkyl radical; as well as the pharmacologically acceptable salts thereof.

The present invention also provides processes for the preparation of these compounds, as well as pharmaceutical compositions containing them.

20 Claims, No Drawings

CARBOXYLIC ACID DERIVATIVES, PROCESSES FOR THE PREPARATION THEREOF AND PHARMACEUTICAL COMPOSITIONS CONTAINING THEM

The present invention is concerned with new carboxylic acid derivatives, processes for the preparation thereof and pharmaceutical compositions containing them.

The new carboxylic acid derivatives according to the present invention are compounds of the general formula:

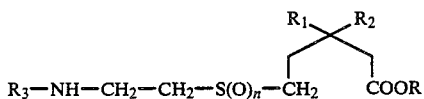

wherein R is a hydrogen atom, alkyl, a metal cation or an ammonium or alkylammonium ion, $R_1$ is a hydrogen atom, a hydroxyl group, an alkyl or an O-alkyl, O-benzyl or O-acyl radical, $R_2$ is a hydrogen atom or an alkyl, aryl or aralkyl radical, n is 0, 1 or 2 and $R_3$ is an acyl radical, this radical being (a) a straight-chained or branched, saturated or unsaturated radical containing 2 to 11 carbon atoms or (b) the radical

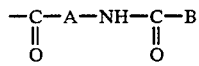

in which A is a straight-chained or branched, saturated or unsaturated aliphatic hydrocarbon chain containing up to 4 carbon atoms, which is optionally substituted by hydroxyl and B is a straight-chained or branched, saturated or unsaturated aliphatic hydrocarbon radical containing up to 8 carbon atoms, which is optionally substituted one or more times by hydroxyl, carboxyl or phenyl, or B is a phenyl or cycloalkyl radical; or (c) the radical

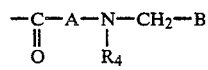

in which A and B have the same meanings as in (b) and $R_4$ is a hydrogen atom or an alkyl or aralkyl radical;

as well as the pharmacologically acceptable salts thereof.

The alkyl radicals in the definitions of the substituents R, $R_1$, $R_2$ and $R_4$ are to be understood straight-chained and branched radicals containing up to 4 carbon atoms, the methyl and ethyl radicals being preferred.

The same applies to the O-alkyl substituents. For the case in which $R_1$ is an O-acyl radical, acyl means the acid residue of an aliphatic or araliphatic carboxylic acid, acetyl, propionyl and butyryl radicals being preferred.

When $R_2$ signifies an aryl radical, this is preferably a phenyl radical which can optionally be substituted, for example, by halogen or methoxy.

Saturated alkanoyl radicals of the substituent $R_3$ are preferably acetyl, propionyl and heptanoyl radicals and preferred unsaturated radicals include propenoyl.

By cycloalkyl radicals in the definition of B are to be understood radicals containing 3 to 7 carbon atoms, the cyclopropyl, cyclopentyl and cyclohexyl radicals being preferred.

By an aralkyl radical in the case of the substituents $R_2$ and $R_4$, there are preferably to be understood the benzyl and phenethyl radicals.

The symbol A used in the description of the radical $R_3$ preferably means $-CH_2-$, $-(CH_2)_2-$, $-(CH_2)_3-$,

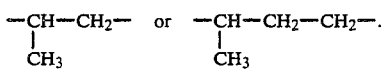

B preferably means $-CH_3$, $-CH_2-CH_3$, $-CH_2-CH_2-CH_3$,

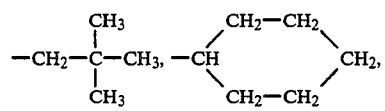

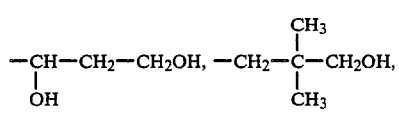

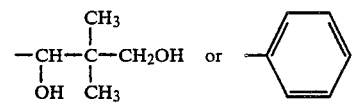

$R_4$ preferably means a methyl, ethyl, propyl or benzyl radical.

The above definitions of the compounds according to the present invention are also to be understood to include all possible stereoisomers, as well as mixtures thereof.

From the literature, there are known some thioethers containing the partial structure of coenzyme A, which function as substrate or inhibitor for certain enzymes.

Thus, the compound 3,4-dicarboxy-3-hydroxybutyl-coenzyme A exerts an inhibiting action on the enzyme citrate synthase (see Angew. Chem., 92, 133/1980).

A structurally similar thioether, namely 3-oxobutyl-coenzyme A, has been described as a substrate for HMG-CoA synthase (see J. Biol. Chem., 257, 2842/1982).

Furthermore, it is known that 3-hydroxy-3-methyl-4-carboxybutyl-coenzyme A possesses an inhibiting action on the enzyme HMG-CoA-reductase (see FEBS Letters, 128, 145/1981).

We have now found that sulphur-substituted pentane-carboxylic acids of general formula (I), which are thus structurally considerably simpler than the above-mentioned compounds, also bring about an inhibition of HMG-CoA-reductase and, in addition, possess good lipid-sinking properties. Consequently, the new compounds according to the present invention can be used for combating increased lipid contents in blood.

The carboxylic acids of general formula (I) can be prepared in that, in per se known manner, (a) a compound of the general formula:

$$R_3-NH-CH_2-CH_2-X \quad (II)$$

is reacted with a compound of the general formula:

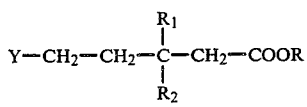

$$Y-CH_2-CH_2-\underset{\underset{R_2}{|}}{\overset{\overset{R_1}{|}}{C}}-CH_2-COOR \quad (III)$$

wherein R, $R_1$, $R_2$ and $R_3$ have the same meanings as above and X and Y represent reactive residues, with the proviso that one of the two residues must be an —SH group; or (b) a compound of the general formula:

$$R_3-NH-CH_2-CH_2-X \quad (II)$$

is reacted with a compound of the general formula:

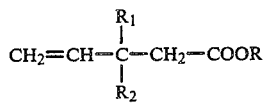

$$CH_2=CH-\underset{\underset{R_2}{|}}{\overset{\overset{R_1}{|}}{C}}-CH_2-COOR \quad (IV)$$

wherein R, $R_1$, $R_2$ and $R_3$ have the same meanings as given above and X is an —SH group; or (c) a compound of the general formula:

$$R_3-Z \quad (V)$$

is reacted with a compound of the general formula:

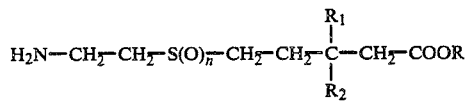

$$H_2N-CH_2-CH_2-S(O)_n-CH_2-CH_2-\underset{\underset{R_2}{|}}{\overset{\overset{R_1}{|}}{C}}-CH_2-COOR \quad (VI)$$

wherein R, $R_1$, $R_2$, $R_3$ and n have the same meanings as above and Z is a reactive group;

subsequently, if desired, a compound of general formula (I) in which n is 0 or 1 is oxidised to a sulphoxide or sulphone and also, if desired, the compound obtained is converted into a pharmacologically acceptable salt.

In process (a), X and Y signify reactive residues, either X or Y thereby being a thiol group but the other residue being a readily substitutable group, for example a halogen atom and especially a chlorine or bromine atom or being an appropriate sulphonic acid ester group, for example mesylate or tosylate. Furthermore, X or Y can also be a phosphoro-organic ester group, for example —O—P(O)Ar$_2$ (cf. Organic Syntheses, 1974, 818).

The reaction of compound (II) with (III) preferably takes place with the addition of an acid-binding agent, for example sodium carbonate or potassium carbonate. However, a more strongly basic agent can also be used, for example sodium hydroxide, potassium hydroxide or barium hydroxide, as well as an alcoholate, such as sodium methylate, sodium ethylate or potassium tert.-butylate, or possibly sodium hydride.

As solvents, there are especially preferred dipolar protic or aprotic solvents, for example methanol, ethanol, propanol, water, acetone, butan-2-one, dimethylformamide, dimethyl sulphoxide, as well as mixtures thereof but, in addition thereto, also non-polar aprotic solvents, for example toluene and tetrahydrofuran.

Furthermore, the reaction can possibly also be carried out in a multi-phase mixture, for example in water/toluene in the case of the presence of a basic agent, such as sodium or potassium hydroxide or potassium carbonate, with the addition of a so-called phase transfer catalyst, for example a tetraalkyl ammonium salt.

It is to be understood that certain further groups present in the molecule which are sensitive towards these methods, such as hydroxyl, amino or carboxyl, must be temporarily protected in appropriate manner, a splitting off of the protective group following the alkylation step.

The addition of a compound of general formula (II) (X=SH) to an olefin (IV) takes place in the desired manner in the presence of a radical chain starter, such as oxygen, a peroxide, azonitrile, metal oxide or metal salt, and with the additional or sole action of UV radiation (cf. Org. Reactions, 13, 150). It is thereby possible to work without solvents or to work in all available inert organic solvents. The reaction temperature is essentially determined by the radical starter used if this is to be thermally split.

The reaction according to process (c) takes place by the reaction of the carboxylic acid derivative (V) with the amino component (VI), which can be used as the free base or as a salt thereof. As reactive derivatives of the carboxylic acids, there are especially preferred the acid chlorides but the esters, azides, anhydrides and mixed anhydrides thereof can be used equally as well.

The reaction is preferably carried out under water-free conditions in an inert solvent, for example dichloromethane or tetrahydrofuran, but, in some cases, also in water or in a two-phase system. As acid-binding agent, there can be used an inorganic or organic basic compound, preferably pyridine, triethylamine, dimethylaminopyridine or ethyldiisopropylamine but also sodium carbonate or sodium hydroxide.

Starting from a sulphide I (n=0), the corresponding sulphoxide I (n=1) is obtained by reaction with a conventional oxidation agent, for example sodium periodate (cf. J. Org. Chem., 27, 282), hydrogen peroxide at a lower temperature, sodium dichromate, nitrogen tetroxide, dimethyl sulphoxide, oxygen or tert.-butyl hypochlorite. Solvents which can be used for this purpose depend upon the solubility of the oxidation agent and include, for example, water, acetone, acetic acid, aliphatic alcohols, benzene or diethyl ether.

For the preparation of the sulphones, there are used oxidation agents such as hydrogen peroxide at an elevated temperature, per acids, potassium permanganate or chromic acid, it being preferable to start from sulphides I (n=0) but possibly from sulphoxides I (n=1). The choice of the reaction conditions and of the reagent depends upon other oxidation-sensitive groups present in the molecule, for example hydroxyl or amino groups, which must possibly be previously protected in known manner.

The esters of general formula I (R=alkyl), which are also within the scope of the present invention, occur either as preliminary stages from which the free carboxylic acids (R=H) are obtained by saponification with a mineral acid or alkali metal hydroxide in a polar solvent, such as water, methanol, ethanol, dioxan or acetone.

The saponification is preferably carried out with a strong base, for example sodium or potassium hydroxide, in a mixture of methanol and water at ambient temperature or at a moderately elevated temperature. On the other hand, however, the carboxylic acids can also be esterified or the esters with a particular radical R can be converted into esters with a different radical R by transesterification. The esterification of the carboxylic acids is preferably carried out in the presence of an acidic catalyst, for example hydrogen chloride, sulphuric acid or p-toluenesulphonic acid, or of a strongly acidic ion exchanger resin. Transesterifications, on the other hand, require the addition of a small amount of a basic substance, for example of an alkali metal or alkaline earth metal hydroxide or of an alkali metal alcoholate. For the esterification of the carboxyl group or for a transesterification, in principle there can be used all alcohols. The lower monohydroxy alcohols are preferred, for example methanol, ethanol or propanol, as well as polyhydroxy alcohols, for example glycerol, or alcohols with other functional groups, for example ethanolamine or glycol ethers.

For the preparation of salts with pharmacologically acceptable organic or inorganic bases, for example sodium hydroxide, potassium hydroxide, calcium hydroxide, ammonium hydroxide, methylglucamine, morpholine or ethanolamine, the carboxylic acids can be reacted with the appropriate bases. Mixtures of carboxylic acids with an appropriate alkali metal carbonate or bicarbonate can also be considered.

For the preparation of compounds (II), the reactive carboxylic acid derivatives (V) are used as starting materials and these are reacted in known manner with appropriate amines, for example aziridine, 2-aminoethanol or 2-aminoethyl bromide, whereby, possibly by a subsequent reaction, the reactive group X must be produced, for example from hydroxyl by exchange for halogen or by conversion into a sulphonic acid ester.

The amide formation takes place in the presence of inorganic or organic acid-binding agents, for example sodium carbonate or triethylamine, preferably in an inert solvent.

For the case in which X=SH, the compounds (V) are reacted in the above-described manner with cystamine (or cystamine dihydrochloride) and the disulphide is split reductively, for example with alkali metal/ammonia, with metals (zinc, aluminium, iron or tin) in acids (acetic acid, hydrochloric acid or sulphuric acid), with alkali metal amalgams or by means of alkali metal sulphides or alkali metal tetrathionates.

Another possibility is the exchange of the reactive group X for SH, whereby here a direct reaction with alkali metal hydrogen sulphides or with sulphur-containing carbonic acid derivatives (for example xanthates, dithiourethanes or isothiouronium salts) or with alkali metal thiosulphates can also take place. In the case of the use of the two last-mentioned methods, there follows a hydrolytic splitting to the thiol, which can take place under acidic or alkaline conditions.

The compounds (III) are obtained from disubstituted glutaric acid derivatives, for example anhydrides, esters or nitriles, whereby, for example, the anhydride can be converted by means of an alkali metal according to the Bouveault-Blanc process, into the hydroxy acid or δ-lactone. This reaction is also possible with complex hydrides and these can also be used for the reduction of the hemiesters.

Conversion of the hydroxy acid or of the δ-lactone into a compound having a reactive residue in the 5-position takes place, for example, with hydrobromic acid/ethanol, phosphorus tribromide, sulphonic acid chloride/base or benzyl triphenoxyphosphonium bromide (Example 1), in which case groups which hinder these methods or which are sensitive towards these methods must possibly be temporarily protected.

For the preparation of (III) (Y=SH), there are used the above-described compounds, the methods for the thiol preparation corresponding essentially to those described for II (X=SH).

The intermediate compound (IV) can be obtained from III (Y≠SH) by β-elimination but, in addition, a synthesis by means of a Claisen rearrangement is also possible (cf. J. Org. Chem., 41, 885) or a hydrolysis of the corresponding dichloroalkene (cf. Chem. Abstracts, 93, 94833u):

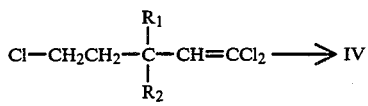

The compounds (VI) used in process (c) are obtainable in the usual manner from III (Y=SH) these being reacted with aziridine or from III (Y≠SH) these being reacted with cysteamine (cf. J.A.C.S., 1947, 770), or with a 2-aminoethylthiol bearing an appropriate amino protective group (n=0), followed if desired by oxidation to sulphoxides (n=1) or to sulphones (n=2).

For the preparation of pharmaceuticals, the compounds of general formula (I) are mixed in the usual way with appropriate pharmaceutical carrier substances, aroma, flavouring and colouring materials and formed, for example, into tablets or dragees or, with the addition of appropriate adjuvants, suspended or dissolved in water or in an oil, for example olive oil.

The compounds of general formula (I) can be administered orally or parenterally in liquid or solid form. As injection medium there is preferably used water which contains the stabilising agents, solubilising agents and/or buffers conventional in the case of injection solutions. Such additives include, for example, tartrate and borate buffers, ethanol, dimethyl sulphoxide, complex formers (such as ethylenediaminetetraacetic acid), high molecular weight polymers (such as liquid polyethylene oxide) for viscosity regulation and polyethylene derivatives of sorbitan-anhydrides.

Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The dosage administered depends upon the age, the state of health and the weight of the recipient, the extent of the disease e.g. high blood cholesterol, the nature of other treatments possibly carried out simultaneously, the frequency of the treatments and the nature of the desired action. The daily dosage of the active compound is usually 0.1 to 50 mg./kg. of body weight. Normally, 0.5 to 40 and preferably 1.0 to 20 mg./kg./day in one or more administrations are effective in order to achieve the desired results.

Preferred within the meaning of the present invention are, apart from the compounds mentioned in the Examples, also the following compounds of general formula (I), as well as their methyl and ethyl esters and the sodium, potassium, calcium and ammonium salts thereof:
1. 9,13-diaza-3,3-dimethyl-10,14-dioxo-6-thiapentadecanoic acid
2. 9,13-diaza-15,17-dihydroxy-3,3-dimethyl-10,14-dioxo-6-thiaheptadecanoic acid
3. 9,13-diaza-17-hydroxy-10,14-dioxo-3,3,16,16-tetramethyl-6-thiaheptadecanoic acid
4. 9,13-diaza-10-oxo-3,3,16,16-tetramethyl-6-thiaheptadecanoic acid
5. 9,13-diaza-13-butyl-3,3-dimethyl-10-oxo-6-thiaheptadecanoic acid
6. 9,13-diaza-13-benzyl-3-ethyl-3-methyl-10-oxo-6-thiapentadecanoic acid
7. 9,13-diaza-15,17-dihydroxy-10-oxo-6-thiaheptadecanoic acid
8. 9,13-diaza-17-hydroxy-10-oxo-3,3,16,16-tetramethyl-6-thiaheptadecanoic acid
9. 9,13-diaza-3-methoxy-3-methyl-10-oxo-14-phenyl-6-thiatetradecanoic acid
10. 9,13-diaza-15,17-dihydroxy-3-methoxy-10,14-dioxo-6-thia-3,16,16-trimethylheptadecanoic acid
11. 9,13-diaza-14-cyclohexyl-3-methyl-10,14-dioxo-3-phenyl-6-thiatetradecanoic acid
11(a) 9,13-diaza-16,16-dimethyl-10,14-dioxo-6-thiaheptadecanoic acid
12. 9,13-diaza-6,10,14-trioxo-3,3,16,16-tetramethyl-6-thiaheptadecanoic acid
13. 9,13-diaza-3,3-dimethyl-6,10,14-trioxo-14-phenyl-6-thiatetradecanoic acid
14. 9,13-diaza-16,16-dimethyl-6,6,10,14-tetraoxo-6-thiaheptadecanoic acid
15. 9,13-diaza-3,14-diphenyl-3-methyl-6,6,10,14-tetraoxo-6-thiatetradecanoic acid Explanation: The raised letters given in the case of the $R_F$ value indicated particular elution agent mixtures:
A: toluene/ethanol = 1/1 v/v
B: acetic acid/n-butanol/water = 15/60/25 v/v/v
C: butyl acetate/isopropanol/water/NH$_3$ = 30/50/15/5 v/v/v/v
D: dichloromethane/acetone = 1/1 v/v
E: chloroform/butan-2-one/methanol/acetic acid/water = 75/25/35/5/9 v/v/v/v/v The stationary phase used was silica gel.

The following Examples are given for the purpose of illustrating the present invention:

EXAMPLE 1

5-Bromo-3-hydroxy-3-methylpentanoic acid methyl ester

To a solution of 3.00 g. (18.5 mmol) 3,5-dihydroxy-3-methylpentanoic acid methyl ester in 15 ml. anhydrous tetrahydrofuran is added a solution of 8.90 g. (18.5 mmol) benzyl triphenoxyphosphonium bromide in 10 ml. tetrahydrofuran and the reaction mixture is stirred for 15 hours at ambient temperature. Thereafter, it is evaporated in a vacuum, the bath temperature thereby being kept below 15° C. The oily residue obtained is chromatographed on 700 g. silica gel 60 with n-hexane/tert.-butanol (6:1 v/v) as elution agent. After removal of the elution agent, there is obtained 1.32 g. (32% of theory) of the desired product in the form of a bright yellow oil; $n_D^{20}$=1.4734; $R_F$=0.65 (silica gel; n-hexane/tert.-butanol (6:1 v/v)).

IR (film): 3500 (OH), 2950–2970 (CH), 1725 (C=O), 1200 (c—O), 650 cm$^{-1}$ (C—Br).

$^1$H—NMR (CCl$_4$): δ=1.2 (s; 3H), 2.0 (t, J=3 Hz; 2H), 2.4 (s; 2H), 3.4 (t, J=3 Hz; 2H), 3.7 (s; 3H).

EXAMPLE 2

9,13-Diaza-10,14-dioxo-6-thia-3,15,17-trihydroxy-3,16,16-trimethylheptadecanoic acid A solution of 17.8 mg. (0.10 mmol) 3,7-diaza-9,11-dihydroxy-10,10-dimethyl-4,8-dioxoundecanethiol and 125 mg. (0.55 mmol) 5-bromo-3-hydroxy-3-methylpentanoic acid methyl ester in 10 ml. of 50% methanolic 0.25M sodium carbonate—0.1N sodium hydroxide solution is stirred for 5 hours under an atmosphere of nitrogen. The reaction mixture is then evaporated and the residue is purified by column chromatography on DEAE-Sepharose with a lithium chloride gradient elution (linear; 0–0.2 molar). There are obtained 20 mg. (49% of theory) of the desired product in the form of a very hygroscopic solid; $R_F$=0.49 (silica gel; acetic acid/n-butanol/water = 15/60/25 v/v/v).

EXAMPLE 3

9-Aza-3-hydroxy-3-methyl-10-oxo-6-thiaheptadecanoic acid

A solution of 406 mg. (2.00 mmol) N-octanoylcysteamine and 426 mg. (2.10 mmol) 5-bromo-3-hydroxy-3-methylpentanoic acid in 50 ml. of 50% methanolic 0.2N sodium hydroxide solution is stirred under an atmosphere of nitrogen for 8 hours, then acidified and extracted with ethyl acetate. The residue obtained after drying the organic phase with anhydrous sodium sulphate and evaporating is recrystallised several times from methanol/diethyl ether. There are obtained 275 mg. (40% of theory) of the desired compound; m.p. 99° C.; $R_F$=0.72 (silica gel; acetic acid/n-butanol/water = 15/60/25 v/v/v/).

EXAMPLE 4

5-Bromo-3-methylpentanoic acid ethyl ester

A solution of 16.0 g. (0.14 mol) 4-methyl-3,4,5,6-tetrahydro-2-pyranone in 50 ml. anhydrous ethanol is saturated with hydrogen bromide gas at 0°–5° C., left to stand overnight, poured into water and extracted with diethyl ether. The combined ether extracts are dried over anhydrous sodium sulphate and evaporated and the residue is distilled in a vacuum to give 21.9 g. (70% of theory) of the desired product in the form of a colourless liquid; b.p. 85°–87° C./0.1 mm.; $n_D^{20} = 1.4590$.

$^1$H—NMR (CDCl$_3$): $\delta$ = 0.98 (d, J = 6 Hz; 3H), 1.29 (t, J = 7 Hz; 3H), 1.67–2.16 (mc; 3H), 2.25 (s, broad; 2H), 3.45 (t, J = 7 Hz; 2H), 4.15 (q, J = 7 Hz; 2H).

The following compounds are prepared in an analogous manner:

(4a) from 4-ethyl-4-methyl-3,4,5,6-tetrahydro-2-pyranone and methanol.

5-bromo-3-ethyl-3-methyl-pentanoic acid methyl ester.

yield: 75% of theory; b.p. 56°–8° C./0.01 mm; $n_D^{20} = 1.4608$.

$^1$H-NMR (CDCl$_3$): $\delta$ = 0.85 (t, J = 7 Hz; 3H), 1.00 (s; 3H), 1.37 (q, J = 7 Hz; 2H), 1.73–2.13 (m; 2H), 2.2 (s; 3H), 3.22–3.58 (m; 2H), 3.65 (s; 3H).

(4b) from 4-phenyl-3,4,5,6-tetrahydro-2-pyranone and ethanol.

5-bromo-3-phenyl-pentanoic acid ethyl ester.

yield: 89% of theory; b.p.: 126°–31° C./0.1 mm; $n_D^{20} = 1.5216$.

$^1$N-HMR (CDCl$_3$): $\delta$ = 1.13 (t, J = 7 Hz; 3H), 2.05–2.40 (t, J = 6.5 Hz; 2H), 2.61 (d, J = 7.5 Hz; 2H), 2.97–3.55 (m; 3H), 4.06 (q, J = 7 Hz; 2H), 7.27 (s; 5H)..

(4c) from 4-methyl-4-phenyl-3,4,5,6-tetrahydro-2-pyranone and ethanol.

5-bromo-3-methyl-3-phenyl-pentanoic acid ethyl ester.

yield: 80% of theory; b.p.: 151°–5° C./0.1 mm; $n_D^{20} = 1.5289$.

$^1$H-NMR (CDCl$_3$): $\delta$ = 1.08 (t, J = 7 Hz; 3H), 1.52 (s, 3H), 2.00–2.55 (m; 2H), 2.64 (s; 2H), 2.82–3.34 (m; 2H), 4.00 (q, J = 7 Hz; 2H), 7.3 (s; 5H).

(4d) from 5,6-dihydro-2-pyranone and ethanol.

5-bromo-3-ethoxy-pentanoic acid ethyl ester.

yield: 23% of theory; b.p.: 64° C./0.02 mm; $n_D^{20} = 1.4560$.

$^1$H-NMR (CDCl$_3$): 67 = 1.18 (t, J = 7 Hz; 3H), 1.26 (t, J = 7 Hz; 3H), 2.00–2.14 (m; 2H), 2.38–2.66 (m; 2H), 3.42–3.66 (m; 4H), 3.86–3.96 (m; 1H), 4.14 (q. J = 7 Hz; 2H).

EXAMPLE 5

3,7-Diaza-7-(tert.-butoxycarbonyl)-4-oxo-8-phenyloctanethiol

To a solution of 5.61 g. (20.0 mmol) 4-aza-4-(tert.-butoxycarbonyl)-5-phenylpentanoic acid in 60 ml. anhydrous dichloromethane and 2.02 g. (20.0 mmol) triethylamine are added, within the course of 30 minutes at −10° C., 2.73 g. (20.0 mmol) chloroformic acid isobutyl ester. The reaction mixture is stirred for 30 minutes and, again at −10° C.; a solution of 2.27 g. (20.0 mmol) 2-aminoethanethiol in 60 ml. dichloromethane is added dropwise thereto. Subsequently, the reaction mixture is allowed to warm up to ambient temperature within the course of 1 hour, then filtered with suction and the filtrate washed with water and an aqueous solution of sodium bicarbonate. The organic phase is dried over anhydrous sodium sulphate and evaporated to give 6.3 g. (94% of theory) of the desired product in the form of a colourless oil which is further reacted without purification; $R_F^B = 0.92$; $R_F^3 = 0.88$.

In an analogous manner and using tetrahydrofuran as solvent, from 4-aza-7,7-dimethyl-6-hydroxy-9-oxa-5-oxo-10,10,10-triphenyldecanoic acid there is obtained:

(5a) 3,7-aza-10,10-dimethyl-9-hydroxy-12-oxa-4,8-oxo-13,13,13-triphenyltridecanethiol.

yield: 45% of theory; m.p. 63° C. (decomp.); from 4-aza-4-methyl-5-cyclohexylpentanoic acid.

(5b) 3,7-aza-8-cyclohexyl-7-methyl-4-oxo-octanethiol.

yield: 39% of theory; precipitated as oxalate; m.p. 119°–121° C. (recrystallised from ethanol); from 4-aza-4-(tert.-butoxycarbonyl)-6,6-dimethylheptanoic acid.

(5c) 3,7-aza-7-(tert.-butoxycarbonyl)-9,9-dimethyl-4-oxo-decanethiol.

yield: 90% of theory; oil; $R_F^A = 0.89$; $R_F^B = 0.83$. from 4-aza-4-butyl-octanoic acid and using dichloromethane as solvent.

(5d) 3,7-aza-7-butyl-4-oxo-undecanethiol.

yield: 49% of theory; precipitated as oxalate; m.p. 106°–107° C. (recrystallized from isopropanol) $R_F^B = 0.25$; $R_F^C = 0.90$.

EXAMPLE 6

3,7-Diaza-6-methyl-4,8-dioxo-8-phenyloctanethiol

Into a stirred mixture of 5.84 g. (11.0 mmol) bis-(3,7-diaza-6-methyl-4,8-dioxo-8-phenyloctane)disulphide, 50 ml. of 4N sulphuric acid and 20 ml. ethanol there are introduced, within the course of 2 hours, 7.80 g. (0.12 g. atom) of zinc dust, followed by suction filtration and extraction with diethyl ether. The organic phase is dried with anhydrous sodium sulphate and evaporated and the residue obtained is recrystallised from ethanol to give 3.5 g. (58% of theory) of the desired product; m.p. 156°–157° C.

In an analogous manner, from the corresponding disulphides there are obtained the following compounds:

(6a) 3,7-diaza-4,8-dioxo-undecanethiol.

yield: 73% of theory; m.p. 169°–170° C. (stirred up with ligroin).

(6b) 3-aza-4-oxo-hexanethiol.

yield: 85% of theory; oil; $R_F^A = 0.54$; $R_F^B = 0.64$;

(6c) 3,7-diaza-4,8-dioxo-8-phenyloctanethiol.

yield: 73% of theory; m.p. 127°–128° C. (recrystallised from dichloromethane); was continuously extracted with dichloromethane.

(6d) 3,7-diaza-8-cyclohexyl-4,8-dioxooctanethiol yield: 56% of theory; m.p. 118° C. (recrystallised from ligroin/diethyl ether).

(6e) 3,7-diaza-10,10-dimethyl-4,8-dioxoundecanethiol.

yield: 44% of theory; wax; $R_F^A = 0.31$.

In Examples (6c) to (6e), under otherwise the same reaction conditions, 6N hydrochloric acid is used instead of 4N sulphuric acid.

EXAMPLE 7

9,13-Diaza-3,3,-dimethyl-10,14-dioxo-6-thia-heptadecanoic acid ethyl ester

To a stirred solution of sodium ethylate (from 0.46 g.=20.0 mg. atom sodium) in 50 ml. anhydrous ethanol are added, under an atmosphere of nitrogen, 4.37 g. (20.0 mmol) 3,7-diaza-4,8-dioxoundecanethiol. The reaction mixture is subsequently stirred for 15 minutes, 5.22 g. (22.0 mmol) 5-bromo-3,3-dimethylpentanoic acid ethyl ester added thereto and the reaction mixture is heated to 50° to 60° C. for 3 hours. Thereafter, it is evaporated, the residue is taken up in dichloromethane, washed with water and the organic phase dried over anhydrous sodium sulphate and evaporated. The residue is recrystallised from ethyl acetate to give 5.0 g. (67% of theory) of the desired product; m.p. 104°–105° C.; $R_F{}^C$=0.80.

In an analogous manner, from 5-bromo-3,3-dimethylpentanoic acid ethyl ester there are prepared the following compounds:

(7a) with 3,7-diaza-10,10-dimethyl-4,8-dioxoundecanethiol.

9,13-diaza-10,14-dioxo-3,3,16,16-tetramethyl-6-thiaheptadecanoic acid ethyl ester.

yield: 77% of theory; wax-like substance of m.p. 106°–115° C. (recrystallised from diethyl ether/ligroin).
(7b) with 3,7-diaza-4,8-oxo-8-phenyloctanethiol.

9,13-diaza-3,3-dimethyl-10,14-dioxo-14-phenyl-6-thiatetradecanoic acid ethyl ester.

yield: 90% of theory; viscous oil; $R_F{}^A$=0.65; $R_F{}^B$=0.61.
(7c) with 3,7-diaza-8-cyclohexyl-4,8-dioxaoctanethiol.

9,13-diaza-14-cyclohexyl-3,3-dimethyl-10,14-dioxo-6-thiatetradecanoic acid ethyl ester.

yield: 50% of theory; viscous wax; $R_F{}^A$=0.70; $R_F{}^B$=0.68.
(7d) with 3,7-diaza-6-methyl-4,8-dioxo-8-phenyloctanethiol.

9,13-diaza-10,14-dioxo-14-phenyl-6-thia-3,3,12-trimethyltetradecanoic acid ethyl ester.

yield: 31% of theory; m.p. 102°–104° C.; $R_F{}^C$=0.87.
(7e) with 3,7-diaza-7-(tert.-butoxycarbonyl)-4-oxo-8-phenyloctanethiol.

9,13-diaza-13-(tert.-butoxycarbonyl)-3,3-dimethyl-10-oxo-14-phenyl-6-thiatetradecanoic acid ethyl ester.

yield: 95% of theory; oil; $R_F{}^B$=0.83; $R_F{}^C$=0.91; $R_F{}^E$=0.95.

EXAMPLE 8

Analogously to Example 7, by reacting 5-bromopentanoic acid ethyl ester with the appropriate thiols, there are prepared the following compounds:
(8a) with 3-aza-4-oxo-hexanethiol.

9-aza-10-oxo-6-thiadodecanoic acid ethyl ester.

yield: 72% of theory; oil; $n_D{}^{20}$=1.4871; $R_F{}^A$=0.67; $R_F{}^B$=0.63
(8b) with 3,7-diaza-10,10-dimethyl-4,8-dioxo-undecanethiol.

9,13-diaza-16,16-dimethyl-10,14-dioxo-6-thiaheptadecanoic acid ethyl ester.

yield: 71% of theory; wax; $R_F{}^A$=0.75; $R_F{}^B$=0.81.
(8c) with 3,7-diaza-6-methyl-4,8-dioxo-8-phenyloctanethiol.

9,13-diaza-12-methyl-10,14-dioxo-14-phenyl-6-thiatetradecanoic acid ethyl ester.

yield: 93% of theory; m.p. 100°–101° C.

EXAMPLE 9

Analogously to Example 7, by reacting 5-bromo-3-phenylpentanoic acid ethyl ester with the appropriate thiols, there are prepared the following compounds:
(9a) with 3,7-diaza-4,8-dioxooctanethiol.

9,13-diaza-10,14-dioxo-3-phenyl-6-thiaheptadecanoic acid ethyl ester.

yield: 80% of theory; m.p. 77°–80° C. (recrystallised from diethyl ether/ligroin); $R_F{}^A$=0.64; $R_F{}^B$=0.68.
(9b) with 3,7-diaza-6-methyl-4,8-dioxo-8-phenyloctanethiol.

9,13-diaza-3,14-diphenyl-12-methyl-10,14-dioxo-6-thiatetradecanoic acid ethyl ester.

yield: 85% of theory; oil.

EXAMPLE 10

Analogously to Example 7, there are prepared the following compounds:
(10a) from 3,7-diaza-8-cyclohexyl-4,8-dioxooctanethiol and 5-bromo-3-methyl-3-phenylpentanoic acid ethyl ester.

9,13-diaza-14-cyclohexyl-3-methyl-10,14-dioxo-3-phenyl-6-thiatetradecanoic acid ethyl ester yield: 88% of theory; viscous oil; $R_F{}^B$=0.84; $R_F{}^C$=0.78.
(10b) 3,7-diaza-4,8-dioxo-8-phenyloctanethiol and 5-bromo-3-methylpentanoic acid ethyl ester.

9,13-diaza-3-methyl-10,14-dioxo-14-phenyl-6-thiatetradecanoic acid ethyl ester.

yield: 83% of theory; wax; $R_F{}^D$=0.45.
(10c) from 3,7-diaza-7-(tert.-butoxycarbonyl)-4-oxo-8-phenyloctanethiol and 5-bromo-3-ethyl-3-methylpentanoic acid methyl ester.

9,13-diaza-13-(tert.butoxycarbonyl)-3-ethyl-3-methyl-10-oxo-14-phenyl-6-thiatetradecanoic acid methyl ester.

yield: 75% of theory; viscous oil; $R_F{}^B$=0.81; $R_F{}^C$=0.94; $R_F{}^E$=0.93.
(10d) from 3,7-diaza-10,10-dimethyl-9-hydroxy-11-oxa-4,8-dioxo-13,13,13-triphenyltridecanethiol and 5-bromo-3-methyl-3-phenylpentanoic acid ethyl ester.

9,13-aza-15-hydroxy-18-oxo-10,14-dioxo-3,19,19,19-tetraphenyl-6-thia-3,16,16-trimethylnonadecanoic acid ethyl ester.

yield: 64% of theory; m.p. 54° C.; $R_F{}^B$=0.85.

EXAMPLE 11

9,13-Diaza-15,17-dihydroxy-10,14-dioxo-3,3,16,16-tetramethyl-6-thiaheptadecanoic acid ethyl ester.

A mixture of 2.78 g. (10.0 mmol) 3,7-diaza-9,11-dihydroxy-10,10-dimethyl-4,8-dioxoundecanethiol, 2.37 g. (10.0 mmol) 5-bromo-3,3-dimethylpentanoic acid ethyl ester and 1.38 g. (10.0 mmol) potassium carbonate in 50 ml. ethanol is stirred under an atmosphere of nitrogen for 4 hours at 50° C., diethyl ether is added thereto, followed by suction filtration. The filtrate is evaporated and the residue is worked up several times with ligroin:

yield: 3.2 g. (75% of theory); viscous wax; $R_F^B=0.64$; $R_F^E=0.52$.

From the above thiol, the following compounds are prepared in an analogous manner:

(11a) with 5-bromo-3-methylpentanoic acid ethyl ester.

9,13-diaza-15,17-dihydroxy-10,14-dioxo-6-thia-3,16,16-trimethylheptadecanoic acid ethyl ester.

yield: 96% of theory; wax; $R_F^B=0.79$; $R_F^E=0.72$;

(11b) with 5-bromo-3-ethyl-3-methylpentanoic acid methyl ester.

9,13-diaza-15,17-dihydroxy-3-ethyl-10,14-dioxo-6-thia-3-16,16-trimethylheptadecanoic acid methyl ester.

yield: 31% of theory; wax; $R_F^B=0.80$; $R_F^C=0.75$; $R_F^E=0.71$.

(11c) with 5-bromo-3-methyl-3-phenylpentanoic acid ethyl ester.

9,13-diaza-15,17-dihydroxy-10,14-dioxo-3-phenyl-6-thia-3,16,16-trimethylheptadecanoic acid ethyl ester.

yield: 41% of theory; viscous oil; $R_F^C=0.71$; $R_F^E=0.86$.

(11d) with 5-bromopentanoic acid ethyl ester.

9,13-diaza-16,16-dimethyl-15,17-dihydroxy-10,14-dioxo-6-thiaheptadecanoic acid ethyl ester.

yield: 57% of theory; viscous oil; $R_F^B=0.63$; $R_F^C=0.68$; $R_F^E=0.66$.

(11e) with 5-bromo-3-phenylpentanoic acid ethyl ester.

9,13-diaza-16,16-dimethyl-15,17-dihydroxy-10,14-dioxo-3-phenyl-6-thiaheptadecanoic acid ethyl ester.

yield: 50% of theory; viscous oil; $R_F^B=0.83$; $R_F^C=0.74$; $R_F^E=0.73$.

(11f) with 5-bromo-3-ethoxypentanoic acid ethyl ester.

9,13-diaza-16,16-dimethyl-15,17-dihydroxy-3-ethoxy-10,14-dioxo-6-thiaheptadecanoic acid ethyl ester.

yield: 20% of theory; viscous oil; $R_F^A=0.76$; $R_F^C=0.64$; $R_F^E=0.84$.

(11g) by the reaction of 3,7-diaza-7-(tert.butoxycarbonyl)-9,9-dimethyl-4-oxodecanethiol with 5-bromo-3,3-dimethylpentanoic acid ethyl ester.

9,13-diaza-13-(tert.butoxycarbonyl)-10-oxo-3,3,15,15-tetramethyl-6-thiahexadecanoic acid ethyl ester.

yield: 90% of theory; oil; $R_F^A=0.90$; $R_F^B=0.85$.

(11h) by the reaction of 3,7-diaza-8-cyclohexyl-7-methyl-4-oxo-octanethiol with 5-bromo-3,3-dimethylpentanoic acid ethyl ester.

9,13-diaza-14-cyclohexyl-10-oxo-6-thia-3,3,13-trimethyltetradecanoic acid ethyl ester.

yield: 85% of theory; oil; $R_F^B=0.45$; $R_F^E=0.56$. and by reaction of 3,7-diaza-7-butyl-4-oxo-undecanethiol with 5-bromo-3,3-dimethyl-pentanoic acid ethyl ester (11i) 9,13-diaza-13-butyl-3,3-dimethyl-10-oxo-6-thiaheptanoic acid ethyl ester.

yield: 40% of theory; precipitated as oxalate m.p. 109°–110° C. (recrystallized from ethyl acetate) $R_F^B=0.22$; $R_F^E=0.60$.

EXAMPLE 12

9,12-Diaza-10-oxo-13-phenyl-6-thiatridecanoic acid ethyl ester

To a solution of 6.34 g. (14.0 mmol) 9,12-diaza-12-(tert.butoxycarbonyl)-10-oxo-13-phenyl-6-thiatridecanoic acid ethyl ester in 100 ml. anhydrous tetrahydrofuran are added, with ice-cooling, 150 ml. saturated ethereal hydrochloric acid, followed by stirring for 1 hour at 0° C. and then for 2 hours at ambient temperature. Diethyl ether is added thereto and the precipitate is filtered off with suction to give 4.2 g. (78% of theory) hydrochloride; m.p. 165° C.; $R_F^B=0.59$.

Analogously thereto, there are prepared:

(12a) 9,13-diaza-3,3-dimethyl-10-oxo-14-phenyl-6-thiatetradecanoic acid ethyl ester.

yield: 30% of theory; wax; $R_F^B=0.71$; $R_F^C=0.81$.

(12b) 9,13-diaza-3-ethyl-3-methyl-10-oxo-14-phenyl-6-thiatetradecanoic acid methyl ester.

yield: 40% of theory; wax; $R_F^B=0.73$; $R_F^C=0.86$.

(12c) 9,13-diaza-10-oxo-3,3,15,15-tetramethyl-6-thiahexadecanoic acid ethyl ester.

Only diethyl ether is used as solvent.

yield: 87% of theory; viscous oil; $R_F^A=0.47$; $R_F^B=0.54$.

EXAMPLE 13

8-Amino-6-thiaoctanoic acid ethyl ester

A mixture of 16.2 g. (0.10 mol) 5-thiopentanoic acid ethyl ester and 8.60 g. (0.20 mol) ethyleneimine is stirred for 4 hours at 40° C., then evaporated and rapidly distilled in a vacuum.

Yield: 8.6 g. (42% of theory) of colourless liquid; b.p. 130°–136° C./0.01 mm. $R_F^C=0.49$; $R_F^E=0.39$.

In an analogous manner, from 3-phenyl-5-thiopentanoic acid ethyl ester, there is obtained:

(13a) 8-amino-3-phenyl-6-thiaoctanoic acid ethyl ester.

yield: 94% of theory (not distillable); $R_F^B=0.53$; $R_F^C=0.70$.

EXAMPLE 14

In analogy to the mixed anhydride method described in Example 5, there are obtained the following thiopentanoic acid derivatives:

(14a) by the reaction of 4-aza-7,7-dimethyl-6-hydroxy-9-oxa-5-oxo-10,10,10-triphenyldecanoic acid with 8-amino-3-phenyl-6-thiaoctanoic acid ethyl ester.

9,13-diaza-16,16-dimethyl-15-hydroxy-10,14-dioxo-18-oxa-3,19,19,19-tetraphenyl-6-thianonadecanoic acid ethyl ester.

yield: 87% of theory; wax-like; $R_F^B=0.97$; $R_F^E=0.86$.

(14b) by the reaction of 3-aza-3-(tert.-butoxycarbonyl)-4-phenylbutanoic acid with 8-amino-6-thiaoctanoic acid ethyl ester.

9,12-diaza-12-(tert.-butoxycarbonyl)-10-oxo-13-phenyl-6-thiatridecanoic acid ethyl ester.

yield: 90% of theory; oil; is further worked up crude.

EXAMPLE 15

9,13-Diaza-3,3-dimethyl-10,14-dioxo-6-thiaheptadecanoic acid

A solution of 3.93 g. (10.5 mmol) 9,13-diaza-3,3-dimethyl-10,14-dioxo-6-thiaheptadecanoic acid ethyl ester in 21 ml. 1N aqueous potassium hydroxide solution and 10 ml. ethanol is stirred for 2 hours at 60° C. The ethanol is then distilled off, followed by extraction with dichloromethane and acidification with 2N hydrochloric acid. The aqueous phase is extracted several times with dichloromethane and the organic phase is dried over anhydrous sodium sulphate and evaporated. The residue is brought to crystallisation by trituration with ligroin.

yield 2.6 g. (71% of theory) of the desired product; m.p. 72°–73° C.; $R_F{}^C=0.35$.

In analogous manner, from the corresponding 5-thiopentanoic acid esters, there are prepared the following carboxylic acids:

(15a) 9,13-diaza-10,14-dioxo-3,3,16,16-tetramethyl-6-thiaheptadecanoic acid.

yield: 53% of theory; m.p. 61°–65° C. (recrystallised from ligroin/diethyl ether). $R_F{}^A=0.53$; $R_F{}^B=0.81$.

(15b) 9,13-diaza-3,3-dimethyl-10,14-dioxo-14-phenyl-6-thiatetradecanoic acid.

yield: 19% of theory; m.p. 75°–77° C. (recrystallised from ethyl acetate); $R_F{}^A=0.55$; $R_F{}^B=0.81$.

(15c) 9,13-diaza-14-cyclohexyl-3,3-dimethyl-10,14-dioxo-6-thiatetradecanoic acid.

yield: 21% of theory; m.p. 123° C.; $R_F{}^A=0.68$; $R_F{}^B=0.78$.

(15d) 9,13-diaza-10,14-dioxo-14-phenyl-6-thia-3,3,12-trimethyltetradecanoic acid.

yield: 30% of theory; m.p. 111°–112° C.; $R_F{}^C=0.36$.

(15e) 9-aza-10-oxo-6-thiadodecanoic acid.

yield: 62% of theory; m.p. 45°–47° C. (recrystallised from ligroin/diethyl ether); $R_F{}^A=0.54$; $R_F{}^B=0.64$.

(15f) 9,13-aza-16,16-dimethyl-10,14-dioxo-6-thiaheptadecanoic acid.

yield: 76% of theory; m.p. 74°–77° C. (recrystallised from diethyl ether); $R_F{}^A=0.46$; $R_F{}^B=0.72$.

(15g) 9,13-diaza-12-methyl-10,14-dioxo-14-phenyl-6-thiatetradecanoic acid.

yield: 33% of theory; m.p. 102°–104° C.; $R_F{}^B=0.85$; $R_F{}^C=0.37$.

(15h) 9,13-diaza-10,14-dioxo-3-phenyl-6-thiaheptadecanoic acid.

yield: 62% of theory; m.p. 84°–88° C. (recrystallised from diethyl ether/ligroin); $R_F{}^A=0.47$; $R_F{}^B=0.71$.

(15j) 9,13-diazo-3,14-diphenyl-12-methyl-10,14-dioxo-6-thiatetradecanoic acid.

yield: 40% of theory; m.p. 63°–66° C. (recrystallised from diethyl ether/ligroin); $R_F{}^C=0.38$.

(15k) 9,13-diaza-14-cyclohexyl-3-methyl-10,14-dioxo-3-phenyl-6-thiatetradecanoic acid.

yield: 43% of theory; m.p. 109°–111° C. (recrystallised from diethyl ether); $R_F{}^A=0.57$; $R_F{}^B=0.83$.

(15l) 9,13-diaza-3-methyl-10,14-dioxo-14-phenyl-6-thiatetradecanoic acid.

yield: 78% of theory; m.p. 69°–70° C. (recrystallised from diethyl ether/ligroin); $R_F{}^B=0.80$; $R_F{}^C=0.38$.

(15m) 9,13-diazo-3,3-dimethyl-10-oxo-14-phenyl-6-thiatetradecanoic acid.

yield: 38% of theory; m.p. 97°–99° C.; $R_F{}^B=0.70$; $R_F{}^E=0.58$.

(15n) 9,13-diazo-3-ethyl-3-methyl-14-phenyl-10-oxo-6-thiatetradecanoic acid.

yield: 37% of theory; m.p. 94°–97° C.; $R_F{}^B=0.71$; $R_F{}^E=0.61$.

(15o) 9,13-diaza-15,17-dihydroxy-10,14-dioxo-3,3,16,16-tetramethyl-6-thiaheptadecanoic acid.

yield: 25% of theory; m.p. 73°–83° C.; $R_F{}^B=0.79$; $R_F{}^C=0.34$; $R_F{}^E=0.61$.

(15p) 9,13-diazo-15-hydroxy-18-oxa-10,14-dioxo-3,19,19,19-tetraphenyl-6-thia-3,16,16-trimethylnonadecanoic acid.

yield: 50% of theory; m.p. 56°–57° C.; $R_F{}^B=0.89$.

(15q) 9,13-diaza-16,16-dimethyl-15-hydroxy-18-oxa-10,14-dioxo-3,19,19,19-tetraphenyl-6-thianonadecanoic acid.

yield: 89% of theory; m.p. 62° C. (recrystallised from diethyl ether/ligroin): $R_F{}^E=0.90$.

EXAMPLE 16

9,12-Diaza-10-oxo-13-phenyl-6-thiatridecanoic acid

A solution of 3.89 g. (10.0 mmol) 9,12-diaza-10-oxo-13-phenyl-6-thiatridecanoic acid ethyl ester in 25 ml. 2N hydrochloric acid and 5 ml. dioxan is refluxed for 2 hours, then concentrated to one third, mixed with acetone and cooled. The crystals which separate out are recrystallised from ethanol to give 2.2 g. (61% of theory) of the desired product in the form of the hydrochloride; m.p. 105°–106° C.; $R_F{}^B=0.54$; $R_F{}^E=0.51$.

EXAMPLE 17

9,13-Diaza-15,17-dihydroxy-10,14-dioxo-6-thia-3,16,16-trimethylheptadecanoic acid To a solution of 0.84 g. (2.00 mmol) 9,13-diazo-15,17-dihydroxy-10,14-dioxo-6-thia-3,16,16-trimethylheptadecanoic acid ethyl ester in 10 ml. 0.1M phosphate buffer (pH 8.0) is added at ambient temperature 0.2 ml. (200 units) pigs liver esterase. By the addition of 1N aqueous sodium hydroxide solution, the pH value is subsequently kept between 7.5 and 8.0 until this no longer changes. The reaction mixture is extracted with diethyl ether, acidified to pH 4 and continuously extracted with dichloromethane. After evaporation of the dichloromethane phase, the product obtained is worked up several times with ligroin. There is obtained 0.50 g. (63% of theory) of the desired product; viscous wax; $R_F{}^C=0.35$; $R_F{}^E=0.57$.

The following 5-thiopentanoic acids are obtained in an analogous manner:

(17a) 9,13-diazo-15,17-dihydroxy-16,16-dimethyl-10,14-diazo-3-phenyl-6-thiaheptadecanoic acid.

yield: 50% of theory; viscous oil; $R_F{}^B=0.76$; $R_F{}^C=0.38$; $R_F{}^E=0.61$.

(17b) 9,13-diazo-15,17-dihydroxy-16,16-dimethyl-10,14-dioxo-6-thiaheptadecanoic acid yield: 25% of theory; viscous oil; $R_F{}^C=0.21$; $R_F{}^E=0.49$.

EXAMPLE 18

9,13-Diaza-3,3-dimethyl-6,10,14-trioxo-14-phenyl-6-thiaheptadecanoic acid

To a stirred suspension of 226 mg. (1.04 mmol) sodium periodate in 3 ml. water are added at 0° C. 380 mg. (1.00 mmol) 9,13-diazo-3,3-dimethyl-10,14-dioxo-14-phenyl-6-thiaheptadecanoic acid and 0.2 ml. ethanol, followed by stirring for 20 hours in an ice bath. Thereafter, 5 ml. water are added thereto, followed by suction filtration. The filtrate is extracted with dichloromethane. The residue obtained after evaporation solidifies immediately and is recrystallised from ethyl acetate to give 0.26 g. (66% of theory) of the desired product; m.p. 73°–77° C.; $R_F{}^A=0.17$; $R_F{}^B=0.59$.

In an analogous manner, from the corresponding thioethers there are obtained:

(18a) 9,13-diaza-6,10,14-trioxo-3,3,16,16-tetramethyl-6-thiaheptadecanoic acid.

yield: 52% pf theory; m.p. 143°–144° C. (recrystallised from diethyl ether); $R_F{}^A=0.20$; $R_F{}^B=0.59$.

(18b) 9,13-diazo-6,10,14-trioxo-3-phenyl-6-thiaheptadecanoic acid.

yield: 80% of theory; oil; $n_D{}^{30}=1.5390$; $R_F{}^A=0.14$; $R_F{}^B=0.54$.

EXAMPLE 19

9,13-Diaza-16,16-dimethyl-6,6,10,14-tetraoxo-6-thiaheptadecanoic acid

A solution of 346 mg. (1.00 mmol) 9,13-diazo-16,16-dimethyl-10,14-dioxo-6-thiaheptadecanoic acid in 3.5 ml. acetic acid and 0.32 g. 30% hydrogen peroxide is stirred for 1.5 hours at 90° to 100° C., evaporated in a vacuum and worked up several times with ligroin and diethyl ether; yield: 300 mg. (79% of theory) of the desired product; m.p. 95°–96° C.; $R_F{}^A=0.22$; $R_F{}^B=0.58$.

In an analogous manner, from the corresponding thioethers there are obtained:

(19a) 9,13-diaza-3,14-diphenyl-3-methyl-6,6,10,14-tetraoxo-6-thiatetradecanoic acid.

yield: 84% of theory; viscous oil; $R_F{}^A=0.23$; $R_F{}^B=0.72$.

(19b) 9,13-diaza-6,6,10,14-tetraoxo-3-phenyl-6-thiaheptadecanoic acid yield: 74% of theory; m.p. 116°–117° C.; $R_F{}^A=0.17$; $R_F{}^B=0.61$.

ACTIVITY OF INVENTIVE COMPOUNDS

Experimental

Rat hepatocytes were isolated according to Berry and Friend (J. Cell Biol., 43, 506–520 (1969)) and cultured as described by Davis et al. (J. Biol. Chem., 254, 2010–2016 (1979)). 2-$^{14}$C-Acetate was used as a precursor for determination of the cholesterol biosynthesis. Newly synthetized cholesterol was determined by liquid scintillation spectrometry after extraction of radiolabelled sterols from the culture medium (Can. J. Biochem. Physiol., 37, 912–917 (1959)). The test compounds were dissolved in dimethylsulfoxide. 1 μl of this solution was given to 1 ml of the culture medium. The percentage of inhibition of $^{14}$C-acetate incorporation is related to a solvent treated control.

The compounds listed in the following table were tested with respect to their effect on the rate hepatocytes according to the method mentioned above. The compounds were dissolved in DMSO. 1 μl of this solution was added to 1 ml of the culture medium.

The end concentration was about $10^{-5}$ M, the period of the incubation was 48 h. The $^{14}$C-acetate incorporation in cholesterol was determined.

| Compounds | Acetate-Incorporation Inhibition % |
|---|---|
| 16 | 10% |
| 15 (d) | 12% |
| 11 | 28% |
| 2 | 33% |
| Compactin | 59% |

The results show that the compounds have a significant inhibition of the cholesterol-biosynthesis.

Compactin = 2-Methylbutanoic acid 1,2,3,7,8,8α-hexahydro-7-methyl-8-[2-(tetrahydro-4-hydroxy-6-oxo-2H-pyran-2-yl)ethyl]-1-naphthalenyl ester; is a potent inhibitor of HMG-CoA reductase and used as comparison compound.

It will be understood that the specification and examples are illustrative but not limitative of the present invention and that other embodiments within the spirit and scope of the invention will suggest themselves to those skilled in the art.

What is claimed is:

1. A carboxylic acid derivative of the formula

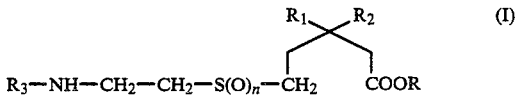

wherein

R is hydrogen, $C_1$–$C_4$ alkyl, a metal cation, or an ammonium or $C_1$–$C_4$ alkylammonium ion, $R_1$ is hydrogen, hydroxyl, $C_1$–$C_4$ alkyl, $C_1C_4$ O-alkyl, O-benzyl or O-acyl which is an acid residue of an aliphatic or araliphatic carboxylic acid, $R_2$ is hydrogen, $C_1$–$C_4$ alkyl, phenyl, phenyl substituted by halogen or methoxy, benzyl or phenethyl, n is 0, 1 or 2, and $R_3$ is an acyl which is (a) a straight-chained or branched, saturated or unsaturated alkanoyl containing 2 to 11 carbon atoms; or (b)

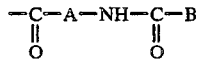

in which A is a straight-chained or branched, saturated or unsaturated aliphatic hydrocarbon containing up to 4 carbon atoms, which is optionally substituted by hydroxyl, and B is a straight-chained or branched, saturated or unsaturated aliphatic hydrocarbon containing up to 8 carbon atoms, which is optionally substituted one or more times by hydroxyl, carboxyl or phenyl, or B is phenyl or $C_3$-$C_7$ cycloalkyl; or (c)

$$-\underset{\underset{O}{\|}}{C}-A-\underset{\underset{R_4}{|}}{N}-CH_2-B$$

in which A and B have the same meanings as in (b) and $R_4$ is hydrogen, or $C_1$-$C_4$ alkyl, benzyl or phenethyl;

or a pharmacologically acceptable salt thereof.

2. The carboxylic acid derivative of claim 1, wherein $R_1$ is hydroxyl or methyl and $R_2$ is methyl.

3. The carboxylic acid derivatives of claim 1 wherein n is 0, R is hydrogen, methyl or ethyl, $R_1$ is hydroxyl or methyl, $R_2$ is methyl and $R_3$ is
—CO—$CH_2$—$CH_2$—NH—CO—CH(OH)—C($CH_3$)$_2$—$CH_2OH$,
—CO—$CH_2$—CH($CH_3$)—NH—CO—phenyl or
—CO—$CH_2$—NH—$CH_2$—phenyl.

4. The compound of claim 3 wherein
R is hydrogen.

5. The compound of claim 3 wherein
R is hydrogen, and
$R_1$ is methyl.

6. The compound of claim 3 wherein
$R_1$ is hydroxyl.

7. The compound of claim 3 wherein
R is methyl or ethyl.

8. The compound of claim 1 wherein
R is hydrogen.

9. The compound of claim 1 wherein
R is hydrogen and
$R_1$ and $R_2$ are methyl.

10. The compound of claim 1 wherein $R_3$ is
—CO—$CH_2$—$CH_2$—NH—CO—CH(OH)—C($CH_3$)$_2$—$CH_2OH$,
—CO—$CH_2$—C($CH_3$)—NH—CO—phenyl or
—CO—$CH_2$—NH—$CH_2$—phenyl.

11. The compound of claim 1 designated 9,13-diaza-10,14-dioxo-6-thia-3,15,17-trihydroxy-3,16,16-trimethylheptadecanoic acid.

12. The compound of claim 1 designated 9,13-diaza-15,17-dihydroxy-10,14-dioxo-3,3,16,16-tetramethyl-6-thiaheptadecanoic acid.

13. The compound of claim 1 designated 9,13-diaza-10,14-dioxo-14-phenyl-6-thia-3,3,12-trimethyltetradecanoic acid.

14. The compound of claim 1 designated 9,12-diaza-10-oxo-13-phenyl-6-thiatridecanoic acid.

15. A method for reducing blood lipids in a patient comprising administering a blood lipid depressing effective amount of a carboxylic acid derivative of the formula:

$$R_3-NH-CH_2-CH_2-S(O)_n-CH_2-\underset{COOR}{\overset{R_1\diagdown\diagup R_2}{\underset{|}{C}}} \quad (I)$$

wherein
R is hydrogen, $C_1$-$C_4$ alkyl, a metal cation, or an ammonium or $C_1$-$C_4$ alkylammonium ion,
$R_1$ is hydrogen, hydroxyl, $C_1$-$C_4$ alkyl, $C_1$-$C_4$ O-alkyl, O-benzyl or O-acyl which is an acid residue of an aliphatic or araliphatic carboxylic acid,
$R_2$ is hydrogen, $C_1$-$C_4$ alkyl, phenyl, phenyl substituted by halogen or methoxy, benzyl or phenethyl,
n is 0, 1 or 2, and
$R_3$ is an acyl which is
(a) a straight-chained or branched, saturated or unsaturated alkanoyl containing 2 to 11 carbon atoms; or $$-\underset{\underset{O}{\|}}{C}-A-NH-\underset{\underset{O}{\|}}{C}-B$$

in which A is a straight-chained or branched, saturated or unsaturated aliphatic hydrocarbon containing up to 4 carbon atoms, which is optionally substituted by hydroxyl, and B is a straight-chained or branched, saturated or unsaturated aliphatic hydrocarbon containing up to 8 carbon atoms, which is optionally substituted one or more times by hydroxyl, carboxyl or phenyl, or B is phenyl or $C_3$-$C_7$ cycloalkyl; or (c)

$$-\underset{\underset{O}{\|}}{C}-A-\underset{\underset{R_4}{|}}{N}-CH_2-B$$

in which A and B have the same meanings as in (b) and $R_4$ is hydrogen, or $C_1$-$C_4$ alkyl, benzyl or phenethyl;

or pharmacologically acceptable salt thereof.

16. The method of claim 15 wherein 0.1 to 50 mg/kg body weight of the compound, are administered daily.

17. The method of claim 16 wherein 0.5 to 40 mg/kg/day are administered.

18. The method of claim 16 wherein 1.0 to 20 mg/kg/day are administered.

19. Pharmaceutical composition containing a blood lipid depressing effective amount of the compound of claim 1 in a pharmaceutically acceptable carrier.

20. The method of claim 15 wherein said compound is selected from the group consisting of
9,13-diaza-10,14-dioxo-6-thia-3,15,17-trihydroxy-3,16,16-trimethylheptadecanoic acid,
9,13-diaza-15,17-dihydroxy-10,14-dioxo-3,3,16,16-tetramethyl-6-thiaheptadecanoic acid,
9,13-diaza-10,14-dioxo-14-phenyl-6-thia-3,3,12-trimethyltetradecanoic acid, and
9,12-diaza-10-dioxo-13-phenyl-6-thiatridecanoic acid.

* * * * *

UNITED STATES PATENT AND TRADEMARK OFFICE
CERTIFICATE OF CORRECTION

PATENT NO. : 4,609,673

DATED : September 2, 1986

INVENTOR(S) : Hermann Eggerer, et al.

It is certified that error appears in the above-identified patent and that said Letters Patent is hereby corrected as shown below:

Column 9, line 53: change "67" to -- 8 --.

Column 10, lines 16, 20, 25 and 31: change "3,7-aza" to

-- 3,7-diaza --.

Column 11, line 34: change "4,8-oxo" to

-- 4,8-dioxo --.

Column 12, line 56: change "9,13-aza" to

-- 9,13-diaza --.

Column 15, line 44: change "9,13-azo" to

-- 9,13-diazo --

Column 16, lines 4, 8, 17, 62 and 66: change "diazo" to

-- diaza --.

UNITED STATES PATENT AND TRADEMARK OFFICE
CERTIFICATE OF CORRECTION

PATENT NO.  :   4,609,673
DATED       :   September 2, 1986
INVENTOR(S) :   Hermann Eggerer, et al.

It is certified that error appears in the above-identified patent and that said Letters Patent is hereby corrected as shown below:

Column 16, line 63: change "diazo" to

-- dioxo --.

Column 17, lines 10, 26 and 35 change "diazo" to

-- diaza --.

Line 24: change "pf" to -- of --.

Signed and Sealed this

Fifteenth Day of September, 1987

Attest:

DONALD J. QUIGG

Attesting Officer      Commissioner of Patents and Trademarks